United States Patent
Apfelbaum et al.

(10) Patent No.: US 10,945,947 B2
(45) Date of Patent: Mar. 16, 2021

(54) FORMULATIONS FOR INTRAVENOUS ADMINISTRATION

(71) Applicant: GLAXOSMITHKLINE INTELLECTUAL PROPERTY (NO.2) LIMITED, Brentford (GB)

(72) Inventors: Rachel Apfelbaum, Collegeville, PA (US); Andrew James Peat, Collegeville, PA (US); Yoon Oh, Collegeville, PA (US)

(73) Assignee: GlaxoSmithKline Intellectual Property (No. 2) Limited

( * ) Notice: Subject to any disclaimer, the term of this patent is extended or adjusted under 35 U.S.C. 154(b) by 0 days.

(21) Appl. No.: 16/701,729

(22) Filed: Dec. 3, 2019

(65) Prior Publication Data

US 2020/0206129 A1    Jul. 2, 2020

Related U.S. Application Data

(63) Continuation of application No. 15/779,611, filed as application No. PCT/IB2016/057220 on Nov. 30, 2016, now abandoned.

(60) Provisional application No. 62/260,727, filed on Nov. 30, 2015.

(51) Int. Cl.
| | |
|---|---|
| A61K 9/08 | (2006.01) |
| A61K 9/19 | (2006.01) |
| A61K 31/4462 | (2006.01) |
| A61K 47/12 | (2006.01) |
| A61K 47/26 | (2006.01) |
| A61K 47/40 | (2006.01) |
| A61K 9/00 | (2006.01) |
| A61K 47/02 | (2006.01) |

(52) U.S. Cl.
CPC .............. *A61K 9/0019* (2013.01); *A61K 9/08* (2013.01); *A61K 9/19* (2013.01); *A61K 31/4462* (2013.01); *A61K 47/02* (2013.01); *A61K 47/12* (2013.01); *A61K 47/26* (2013.01); *A61K 47/40* (2013.01)

(58) Field of Classification Search
CPC .... A61K 31/4462; A61K 47/12; A61K 47/26; A61K 47/40; A61K 9/0019; A61K 9/08; A61K 9/09; A61K 9/19
See application file for complete search history.

(56) References Cited

U.S. PATENT DOCUMENTS

| | | | |
|---|---|---|---|
| 9,809,540 B2 * | 11/2017 | Sanderson | .............. A61P 11/00 |
| 2017/0100385 A1 * | 4/2017 | Washburn | ............... A61P 11/00 |

FOREIGN PATENT DOCUMENTS

WO    WO 2015/173701 A2    11/2015

OTHER PUBLICATIONS

International Search Report for Internal Application No. PCT/IB2016/057220, dated Feb. 28, 2017.

* cited by examiner

*Primary Examiner* — Timothy R Rozof
(74) *Attorney, Agent, or Firm* — Hao Yin

(57) ABSTRACT

The present invention relates to an improved formulation of danirixin in its hydrobromide salt form. This improved formulation can be an aqueous intravenous formulation containing danirixin or a lyophilized pharmaceutical solid composition containing danirixin to be reconstituted to provide a solution for intravenous administration.

14 Claims, No Drawings

FORMULATIONS FOR INTRAVENOUS ADMINISTRATION

FIELD OF THE INVENTION

The present invention relates to pharmaceutical compositions of danirixin for intravenous administration, combinations, kits, and medicaments containing said compositions and methods for treating disease or conditions for which a CXCR2 antagonist is indicated.

BACKGROUND OF THE INVENTION

CXCR2 is a chemokine receptor that is highly expressed on neutrophils, and signaling through this receptor causes inflammatory cell recruitment to the injured tissue. See Morohashi, et al., *Leukocyte Biol,* 1995. 57:180 and McColl, et al., *J. Immunology,* 1999, 163:2829. CXCR2 and some of its ligands (e.g., IL-8), have been shown to be significantly upregulated during inflammatory respiratory conditions in humans. Therefore, compounds which are capable of binding to the CXCR2 receptor and inhibit CXCR2 ligand binding (e.g., IL-8) could help treat conditions associated with an increase in CXCR2 ligand production. Such compounds could, therefore, treat inflammatory conditions associated with CXCR2 ligand induced chemotaxis of neutrophil and T-cells subsets.

Acute viral and bacterial lung infections can cause significant immune inflammation and mucus production, which often leads to clogged airways, difficulty breathing, and hospitalization. Current antiviral treatments and antibiotics work with varying degrees of success when administered shortly after symptom onset. While the infectious agent plays a role in disease and pathogenesis, the overzealous immune response to the infection also significantly contributes to the etiology of severe respiratory illnesses, such as respiratory syncytial virus (RSV) and influenza (IFV).

In particular, mucus overproduction during RSV infection is known to be detrimental to infants because it blocks the small airways of the lungs and prevents proper oxygen exchange. In a mouse model of RSV infection, signaling via CXCR2 contributes to mucus overproduction and airway hyperresponsiveness. Immunoneutralization with an anti-CXCR2 antibody and CXCR2$^{-/-}$ mice showed a significant reduction of mucus in the lungs after RSV infection. Tate, Reading. Plos One. March 2011, Volume 6, Issue 3.

It was also reported that influenza infected mice treated with a CXCR2 ligand antibody (MIP-2), demonstrated reduced lung neutrophil counts along with an improvement in lung pathology without affecting viral replication and clearance. Miller, Lukacs. The *Journal of Immunology,* 2003, 170: 3348-3356. In summary, CXCR2 and some of its ligands (e.g., IL-8), have been shown to be significantly upregulated during respiratory infections in humans. As such, additional medical therapies are needed and could be beneficial that target multiple aspects of a respiratory infection, including, for example, excessive inflammation, mucus overproduction, and airway hyperresponsiveness.

WO 2007/124424 discloses compounds useful in the treatment of disease states mediated by IL-8, including the compound N-{4-chloro-2-hydroxy-3-[-3-piperidinylsulfonyl]phenyl}-N'-(3-fluoro-2-methylphenyl)urea, and the enantiomer N-{4-chloro-2-hydroxy-3-[(3S)-3-piperidinylsulfonyl]phenyl}-V-(3-fluoro-2-methylphenyl)urea; both are referred to herein interchangeably as "danirixin."

Danirixin is a small, high-affinity, selective and reversible CXCR2 antagonist in development for the treatment of chronic obstructive pulmonary disease. Miller, E. et al., *European Journal of Drug Metabolism and Pharmacokinetics* 39.3 (2014): 173-181. Danirixin has demonstrated potent antagonism of CXCR2 activity, both in vitro and in vivo in preclinical studies. Its potency and duration of action support its potential use as an oral anti-inflammatory agent in the treatment of disorders associated with the accumulation of neutrophils. The neutrophil is thought to be an important contributor, via the release of tissue-destructive proteases and other mediators, to excessive mucus production, airway stenosis, and destruction of the lung parenchyma which, in part, is responsible for the decline in lung function associated with chronic obstructive pulmonary disease or COPD. Miller, E. et al., *European Journal of Drug Metabolism and Pharmacokinetics* 39.3 (2014): 173-181.

Danirixin has its highest solubility at pH <2. Therefore, clinical development of orally ingested danirixin has focused on optimizing dissolution in the stomach to deliver a solution of the drug for absorption in the small intestine. A raised intra-gastric pH could have a significant impact on the dissolution and hence absorption of danirixin. Miller, E. et al., *European Journal of Drug Metabolism and Pharmacokinetics* 39.3 (2014): 173-181.

Recently, it was discovered that the hydrobromide salt of danirixin showed improved solubility and dissolution profiles at a higher pH as compared to the free base after oral administration. See International Patent Application Publication No. WO2015071235. Some patients also take proton pump inhibitors, and thus can have a higher than average gastric pH. Such patients would not receive the same exposure to the free base as otherwise healthy patients, and therefore the increased solubility and dissolution of the hydrobromide salt helps increase exposure in such patients.

Thus, it would be advantageous to have available to patients an improved formulation of danirixin hydrobromide salt which can be administered to patients, for example, in a critical care setting, such as, for example, an intravenous formulation. Of course, any such intravenous formulation would have to display sufficient solubility and also chemical and physical stability over the shelf life of the product.

SUMMARY OF THE INVENTION

In one aspect there is provided the pharmaceutical composition of danirixin, or a pharmaceutically acceptable salt thereof; and, one or more pharmaceutically acceptable excipients.

In one aspect there is provided the hydrobromide salt of danirixin, also referred to as N-{4-chloro-2-hydroxy-3-[-3-piperidinylsulfonyl]phenyl}-N'-(3-fluoro-2-methylphenyl)urea, particularly the hydrobromide salt of the enantiomer of danirixin, also referred to as N-{4-chloro-2-hydroxy-3-[(3S)-3-piperidinylsulfonyl]phenyl}-V-(3-fluoro-2-methylphenyl)urea.

In one aspect there is provided pharmaceutically acceptable excipients selected from one or more of sulfobutyl ether-β-cyclodextrin (CAPTISOL®), mannitol, and a citrate buffer.

In one aspect there is provided a pharmaceutical composition comprising danirixin as its hydrobromide salt, sulfobutyl ether-β-cyclodextrin (CAPTISOL®), mannitol, and a citrate buffer wherein the pH is about 4 when reconstituted in water.

In one aspect there is provided a pharmaceutical composition comprising danirixin as its hydrobromide salt, sulfobutyl ether-β-cyclodextrin (CAPTISOL®), mannitol, and a citrate buffer, which is freeze-dried to form a lyophilized powder.

In one aspect there is provided a pharmaceutical composition comprising danirixin as its hydrobromide salt, sulfobutyl ether-β-cyclodextrin (CAPTISOL®), mannitol, and a citrate buffer for use as an intravenous therapy.

In one aspect there is provided a pharmaceutical composition comprising danirixin as its hydrobromide salt, sulfobutyl ether-β-cyclodextrin (CAPTISOL®), mannitol, and a citrate buffer for use as an intravenous therapy to treat symptoms arising from infectious diseases.

In one aspect there is provided a pharmaceutical composition comprising danirixin as its hydrobromide salt, sulfobutyl ether-β-cyclodextrin (CAPTISOL®), mannitol, and a citrate buffer for use as an intravenous therapy to treat symptoms arising from respiratory tract infectious diseases.

DETAILED DESCRIPTION OF REPRESENTATIVE EMBODIMENTS

Throughout this application, references are made to various embodiments relating to compounds, and compositions. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

It is to be understood that the terminology used herein is for the purpose of describing particular embodiments only and is not intended to limit the scope of the present invention. In this specification and in the claims that follow, reference will be made to a number of terms that shall be defined to have the following meanings.

"Compound", "compounds", "chemical entity", and "chemical entities" as used herein refers to a compound encompassed by the generic formulae disclosed herein, any subgenus of those generic formulae, and any forms of the compounds within the generic and subgeneric formula, including the racemates, stereoisomers, and tautomers of the compound or compounds.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "excipient" means the substances used to formulate active pharmaceutical ingredients (API) into pharmaceutical formulations. Excipients (e.g., mannitol, sulfobutyl ether-β-cyclodextrin (CAPTISOL®), lactose, starch, magnesium stearate, sodium saccharine, talcum, cellulose, sodium crosscarmellose, glucose, gelatin, sucrose, magnesium carbonate, and the like) are an intergral part of pharmaceutical development and help to achieve the desired product profile including but not limited to an aid in manufacturing, modify a drug's stability, and efficacy. Acceptable excipients are non-toxic and do not adversely affect the therapeutic benefit of at least one chemical entity described herein. Such excipient may be any solid, liquid, semi-solid or, in the case of an aerosol composition, gaseous excipient that is generally available to one of skill in the art.

Further the term "excipient" encompasses solubilizing agents, stabilizers, carriers, diluents, bulking agents, pH buffering agents, tonicifying agents, antimicrobial agents, wetting agents, and emulsifying agents (e.g., sodium acetate, sodium citrate, cyclodextrine derivatives, sorbitan monolaurate, triethanolamine acetate, triethanolamine oleate, and the like). Preferably, excipients are approved for or considered to be safe for human and animal administration. Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see Remington's Pharmaceutical Sciences, Mack Publishing Company, Easton, Pa.

As used here in, "lyophilization", "lyophilized," and "freeze-dried" refers to a process by which the material to be dried is first frozen and then the ice or frozen solvent is removed by sublimation in a vacuum environment. The term "lyophilized powder" or "lyophilized preparation" refers to any solid material obtained by lyophilization, i.e., freeze-drying of an aqueous solution. The aqueous solution may contain non-aqueous solvents, i.e. a solution composed of aqueous and one or more non-aqueous solvent(s). Preferably, a lyophilized preparation is one in which the solid material is obtained by freeze-drying a solution composed of water as a pharmaceutically acceptable excipient.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Used herein, the term "pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002

The skilled artisan will appreciate that pharmaceutically acceptable salts of compounds may be prepared. These pharmaceutically acceptable salts may be prepared in situ during the final isolation and purification of the compound, or by separately reacting the purified compound in its free acid or free base form with a suitable base or acid, respectively.

Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutical composition" describes a compound and one or more pharmaceutically acceptable excipients. The excipient(s) must be acceptable in the sense of being compatible with the other ingredients of the composition and not deleterious to the recipient thereof. In accordance with another aspect of the invention there is also provided a process for the preparation of a pharmaceutical composition including the agent, or pharmaceutically acceptable salts thereof, with one or more pharmaceutically acceptable excipients. The pharmaceutical compositions can be for use in the treatment and/or prophylaxis of any of the conditions described herein.

Pharmaceutical compositions adapted for parental administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

"Racemates" refers to a mixture of enantiomers. In an embodiment of the invention, danirixin, or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

Such compounds of the present invention can exist in particular geometric or stereoisomeric forms. The invention contemplates all such compounds, including (−)- and (+)- enantiomers, (R)- and (S)-enantiomers, (D)-isomers, (L)- isomers, the racemic mixtures thereof, and other mixtures thereof, such as enantiomerically enriched mixtures, as falling within the scope of the invention. Additional asymmetric carbon atoms can be present in a substituent such as an alkyl group. All such isomers, as well as mixtures thereof, are intended to be included in this invention.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease or symptoms thereof.

Danirixin

Danirixin is a CXCR2 inhibitor currently in Phase 2 clinical trials in the United States for Chronic Obstructive Pulmonary Disease (COPD). Danirixin is described in U.S. Pat. No. 7,893,089, which patent is hereby incorporated by reference in its entirety. International Patent Application Publication No. WO2015071235 relates to hydrobromide salt forms of danirixin. Danirixin has the chemical name: N-{4-chloro-2-hydroxy-3-[3-piperidinylsulfonyl]phenyl}- N'-(3-fluoro-2-methylphenyl)urea, or also, referred to interchangeably herein, as its enantiomer N-{4-chloro-2-hydroxy-3-[(3S)-3-piperidinylsulfonyl]phenyl}-N'-(3-fluoro-2-methylphenyl)urea.

It is intended that for the preparation of intravenous formulations of danirixin, that the therapeutically active compound (danirixin) be present in a concentration of from 0.5 to 90% by weight of the complete mixture. However, it has emerged that the low solubility in water and instability of the free base form of danirixin stand in the way of a conventional formulation of danirixin to give preparations which can be used intravenously. Various approaches were taken in the pursuit of a stable formulation of danirixin that would be useful for intravenous delivery of sufficient bioavailability, stability, and other pharmaceutically desired characteristics. Such improvements to the intravenous formulation of danirixin are described in more detail within Examples 1 to 4, below.

It is found that the present formulations/compositions of danirixin for intravenous administration, which contain danirixin as its hydrobromide salt and pharmaceutically acceptable excipient(s) demonstrates advantages over other intravenous formulations which make it particularly suitable for use in treating certain diseases, for example in, viral infections, or viral respiratory infections, or influenza infections, or RSV infections, or treating exacerbations of any of such diseases.

Specifically the hydrobromide salt IV formulation demonstrates improved stability and decreased amounts of sulfobutyl ether-β-cyclodextrin (CAPTISOL®) as compared to the free base IV formulation. As such, in accordance with one embodiment of the present invention, there is provided danirixin having the structure of Formula I:

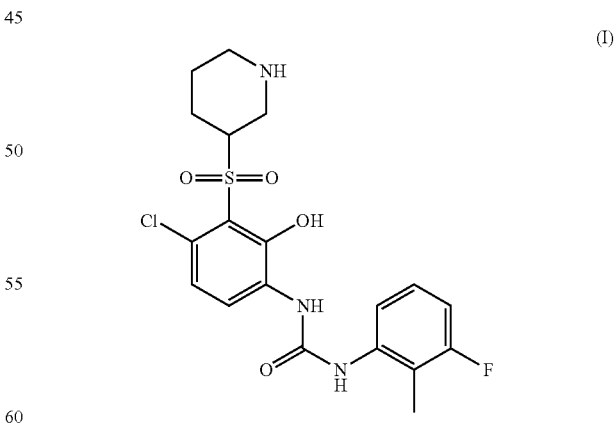

(I)

or a pharmaceutically acceptable salt. In some embodiments, the pharmaceutically acceptable salt is the hydrobromide salt.

In accordance with another embodiment of the present invention, there is provided danirixin having the structure of Formula II:

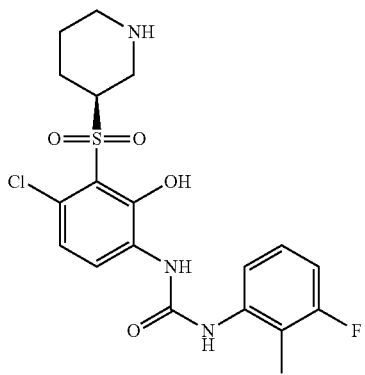

(II)

or a pharmaceutically acceptable salt. In some embodiments, the pharmaceutically acceptable salt is the hydrobromide salt.

Therefore, for purposes of the present invention, the term "danirixin" can refer to the racemate form or the chiral form, both indicated above.

In an alternate embodiment, there is also provided danirixin in the form of a hydrobromide salt as a standalone novel compound with certain excipients described herein and as a parenteral formulation. In addition, such hydrobromide salt of danirixin may be used with the novel therapies and combinations of the present invention.

In another embodiment, there is provided a pharmaceutical composition comprising a therapeutically effective amount of the compound of danirixin, or a pharmaceutically acceptable salt thereof, and one or more pharmaceutically acceptable excipients.

Cyclodextrins, and their derivatives, are able to enhance the aqueous solubility of certain compounds, for example, as taught in U.S. Pat. No. 5,134,127. However, this reference is silent as to whether or not cyclodextrins can enhance the aqueous solubility of danirixin, or any related such CXCR2 inhibitor compounds.

CAPTISOL® is a trade name for a sulfobutyl ether-β-cyclodextrin shown below, and marketed by Ligand Pharmaceuticals, Inc., Lenexa, Kans. Sulfobutyl ether-β-cyclodextrin (CAPTISOL®) is used as a complexing agent to improve the solubility and/or stability of pharmaceutical compounds. The chemical structure of sulfobutyl ether-β-cyclodextrin (CAPTISOL®) is as follows:

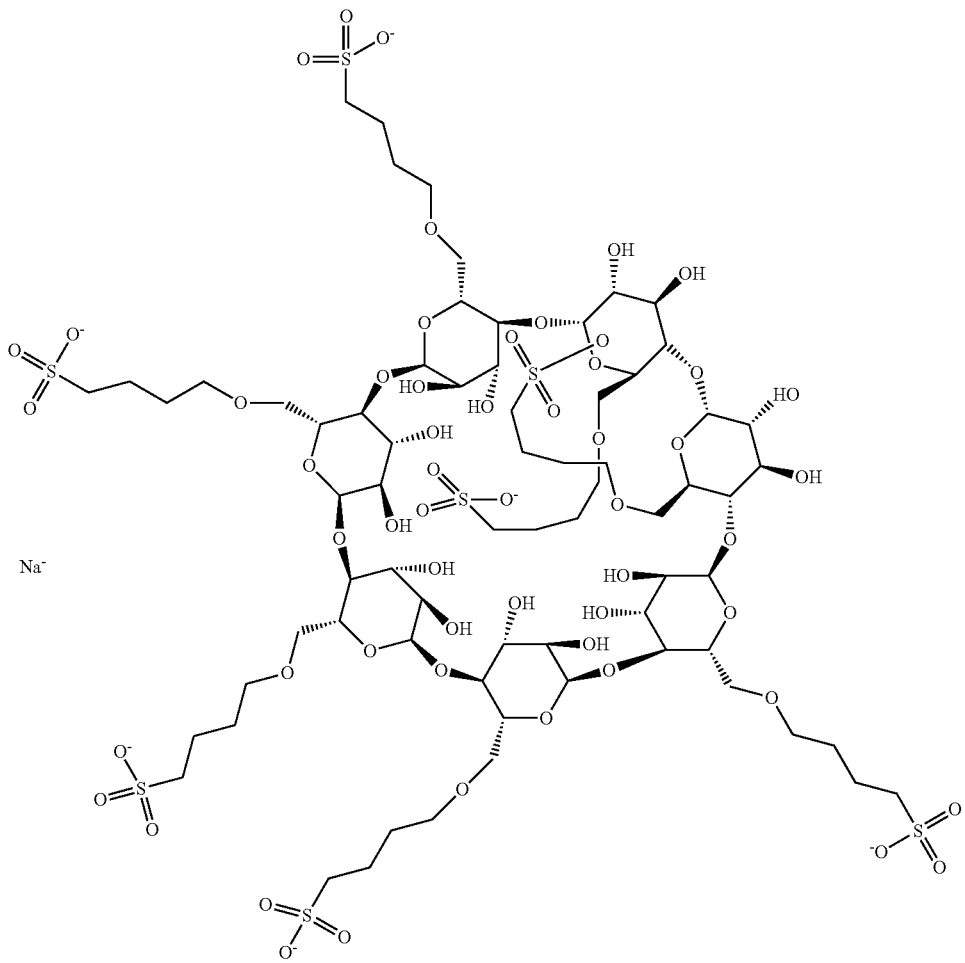

Table 1 displays certain relevant information regarding sulfobutyl ether-β-cyclodextrin (CAPTISOL®).

TABLE 1

| Names | Sulfobutyl ether-β-cyclodextrins, (SBE-β-CD) sodium salt |
|---|---|
| CAS no. | 182410-00-0 |

Mannitol is also known as D-mannitol. It is a hexahydric alcohol related to mannose and is isomeric with sorbitol. It has a CAS registry number of 69-65-8 and has a molecular weight of 182.17. Mannitol is widely used in pharmaceutical formulations. It is generally inert and once freeze dried, rehydrates rapidly. One of these uses includes lyophilization preparations where it is used as a carrier to produce a stiff and homogeneous cake. Mannitol belongs to a class of bulking agents which provide a stable elegant structure to a lyophile. Common bulking agents include mannitol, sorbitol, sucrose, trehalose and amino acids like glycine, histidine, and arginine. These bulking agents can also serve as stabilizer and tonicity adjustment agents. Amongst these bulking agents mannitol and glycine tend to crystallize and provide structural integrity to the lyophile. The chemical structure of mannitol is as follows:

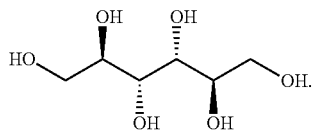

Buffering agents control pH to avoid degradation of the drug during processing, storage and reconstitution, thereby being an important agent in lyophilized formulations. The choice of buffers can depend on the pH stability profile of active ingredients. Ideal buffering agents should possess properties including, but not limited to, a high collapse temperature, non-volatility, and the ability to remain amorphous during lyophilization. The previously mentioned properties would facilitate a faster drying process and would prevent pH drift which can lead to degradation of active components. One such buffering agent, citrate buffer was found to remain amorphous which kept the shift in pH to a minimum. Therefore, in one embodiment, a suitable buffer for the formulations (or pharmaceutical compositions, used interchangeably herein) of the present invention is citrate.

In another embodiment of the invention, the pharmaceutical composition comprises pharmaceutically acceptable excipients, which further comprise sulfobutyl ether-β-cyclodextrin (CAPTISOL®).

In another embodiment of the invention, the pharmaceutically acceptable excipients include sulfobutyl ether-β-cyclodextrin (CAPTISOL®) and mannitol.

In another embodiment of the invention, the pharmaceutically acceptable excipients include one or more of sulfobutyl ether-β-cyclodextrin (CAPTISOL®), mannitol, and a citrate buffer.

In another embodiment of the invention, the pharmaceutical composition has a pH in the range of 3.5 to 4.5.

In another embodiment of the invention, the pharmaceutical composition has the pH of about 4.0.

In another embodiment of the invention, the pharmaceutical composition described herein is freeze-dried to form a lyophilized powder.

As described herein, a lyophilized formulation of danirixin is achieved following removal of solvents from the solution. Typically water is used as solvent; however other organic solvents could be used individually or in combination. The employed solvents must form stable solutions with danirixin and must not appreciably degrade or deactivate the drug substance. Additionally, the solvent should be capable of being removed easily from an aqueous dispersion or solution of the drug product, e.g., through lyophilization or vacuum drying.

A typical formulation and lyophilization cycle useful in accordance with the present invention is provided below. Lyophilization can be carried out using standard equipment for lyophilization or vacuum drying. The cycle may be varied depending on the equipment and facilities used for the fill/finish.

In accordance with a typical embodiment of the present invention, an aqueous pre-lyophilization solution or dispersion is first formulated in a pharmaceutically acceptable compounding vessel. The solution is filtered into a sterile container, filled to an appropriate sized vial, partially stoppered and loaded into the lyophilizer. Using lyophilization techniques described herein the solution is lyophilized until desirable moisture content is achieved. The resulting lyophilizaion powder can be readily reconstituted with sterile water for injection, or other suitable carrier, to provide liquid formulations of danirixin, suitable for administration.

The pre-lyophilization solution or dispersion normally is first formulated in a pharmaceutically acceptable carrier by:
1. taking an appropriate aqueous buffer solution and adding water soluble excipient(s) with mixing,
2. adding danirixin hydrobromide to the desired concentrations with mixing,
3. adding 1N NaOH or 1N HCl, as needed, to adjust the pH to about 3.5 to 4.5
4. filling the solution into the appropriate vials before loading into a lyophilizer.

Although the preceding steps are show in a certain order, it is understood that one skilled in the art can change the order of the steps based on requirements.

The pre-lyophilization solution or dispersion can be sterilized prior to lyophilizaion, and is generally preformed by filtration through an appropriate filter. Multiple sterilization filters can be used. Sterilization of the solution of dispersion can be achieved by other methods know in the art, e.g., radiation. Furthermore, terminal sterilization may be used.

In this case, after sterilization, the solution or dispersion is ready for lyophilization. Generally, the filtered solution will be introduced into a sterile receiving vessel, and then transferred to any suitable container or containers in which the formulation may be effectively lyophilized. Usually the formulation is effectively and efficiently lyophilized in the containers in which the product is to be marketed, such as, without limitation, a vial, as described herein and as known in the art.

A typical procedure for use in lyophilizing the pre-lyophilization solutions or dispersions is set forth below. However, a person skilled in the art would understand that modifications to the procedure or process may be made depending on such things as, but not limited to, the prelyophilization solution or dispersion and lyophilization equipment.

Initially, certain danirixin formulations of the present invention are/is placed in a lyophilization chamber under a range of temperatures and then subjected to temperatures well below the solution's freezing point, generally for several hours. Preferably, the temperature will be at or below about −40° C. for about 2 hours. Then the temperature then be increased to at or below −10° C. for about 3 hours, followed by keeping the temperature at or below −40° C. for about 2 hours. The ramp rate during the freezing and annealing phases is 1.5° C./min. After the freezing cycles are complete, the chamber is evacuated with vacuum pumps. Additionally, evacuation of the chamber should continue until a pressure of about 200 millitorr, is obtained. The drying phase is kept at this pressure and 5° C. for about 31 hours and then the temperature is increased to 50° C. for about 5 hours.

The product composition is then warmed under vacuum in the chamber. The pressure of about 200 millitorr is maintained. The warming process will optimally take place very gradually, with a ramp rate of about 1° C./min. During the initial drying, the product temperature should be increased to about 5° C. and maintained for about 31 hours. A secondary drying phase, the temperature is then increased to about 50° C. and is maintained for about 5 hours.

Once the drying cycle is completed, the pressure in the chamber can be slowly released to atmospheric pressure (or slightly below) with sterile, dry-nitrogen gas (or equivalent gas). If the product composition has been lyophilized in containers such as vials, the vials can be stoppered, removed and sealed. Several representative samples can be removed for purposes of performing various physical, chemical, and microbiological tests to analyze the quality of the product.

The lyophilized formulation is typically marketed in pharmaceutical dosage form. The pharmaceutical dosage form of the present invention, although typically in the form of a vial, may be any suitable container, such as ampoules, syringes, co-vials, which are capable of maintaining a sterile environment. Such containers can be glass or plastic, provided that the material does not interact with the danirixin formulation. The closure is typically a stopper, most typically a sterile rubber stopper, preferably a siliconised stopper, which affords a seal. Typically, a vial will contain a lyophilized powder including about 0.5 to about 10 g/vial, preferably about 1 to 5 g/vial, danirixin. Thus, in one embodiment of the present invention, there is provided a kit comprising a lyophilized powder of danirixin, a glass vial and optionally a syringe.

The lyophilized formulations of the present invention may be reconstituted with water, preferably Sterile Water for Injection, or other sterile fluid such as co-solvents, to provide an appropriate solution of danirixin for administration, as through parenteral injection following further dilution into an appropriate intravenous admixture container, for example, including normal saline.

The principles, preferred embodiments, and modes of operation of the present invention have been described in the foregoing specification. The invention which is intended to be protected herein, however, is not to be construed limited to the particular forms disclosed, since these are to be regarded as illustrative rather than restrictive. Variations and changes may be made by those skilled in the art, without departing from the spirit of the invention.

In another embodiment of the invention, the pharmaceutical composition described herein is administered intravenously.

In another embodiment of the invention, the pharmaceutical composition is for use in therapy.

In another embodiment of the invention, the pharmaceutical composition is for use in treating a disease or condition for which a CXCR2 antagonist is indicated.

In another embodiment of the invention, the pharmaceutical composition is for use in treating influenza or RSV.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

These procedures may involve mixing, granulating and compressing or dissolving the ingredients as appropriate to the desired preparation. It will be appreciated that the form and character of the pharmaceutically acceptable excipient is dictated by the amount of active ingredient with which it is to be combined, the route of administration and other well-known variables. The excipient(s) must be "acceptable" in the sense of being compatible with the other ingredients of the formulation and not deleterious to the recipient thereof.

The pharmaceutical excipient employed may be, for example, either a solid or liquid. Exemplary of solid excipients are lactose, terra alba, sucrose, talc, gelatin, agar, pectin, acacia, magnesium stearate, stearic acid and the like. Exemplary of liquid excipients are syrup, peanut oil, olive oil, water and the like. Similarly, the excipient may include time delay material well known to the art, such as glyceryl monostearate or glyceryl distearate alone or with a wax. A wide variety of pharmaceutical forms can be employed. Thus, when a liquid excipient is used, the preparation will be in the form of sterile injectable liquid such as an ampoule or non-aqueous liquid suspension.

In general, the chemical entities provided will be administered in a therapeutically effective amount by any of the accepted modes of administration for agents that serve similar utilities. The actual amount of the chemical entity, i.e., the active ingredient, will depend upon numerous factors such as the severity of the disease to be treated, the age and relative health of the subject, the potency of the chemical entity used, the route and form of administration, and other factors. The drug can be administered more than once a day, such as once or twice a day.

Therapeutically effective amounts of the chemical entity described herein may range from approximately 0.01 to 20 mg per kilogram body weight of the recipient per day; such as about 0.1-10 mg/kg/day, for example, from about 0.5 to 5 mg/kg/day. Thus, for administration to a 70 kg person, the dosage range may be about 10-1000 mg per day.

EXAMPLES

The following examples further describe and exemplify particular embodiments within the scope of the present Invention. The examples are given solely for illustration and are not to be construed as limitations as many variations are possible without departing from spirit and scope of the Invention.

The compound of Formula I and Formula II may be synthesized by one of skill in the art by following the teachings described in U.S. Pat. No. 7,893,089, which is hereby incorporated by reference in its entirety. The HBr salt of Formula I and Formula II may be synthesized by one of skill in the art by following the teachings described in WO 2015/071235.

Example 1

IV Formulation and Stability of Free Base Danirixin

Table A shows the components and respective amount per IV formulation of free base danirixin.

TABLE A

| COMPOSITION | Formula (mg/mL) 2 mg/mL | Unit Formula, Nominal Fill (mg/13 mL) |
|---|---|---|
| Danirixin Free Base. ACTIVE SUBSTANCE | 2.0 mg | 26.0 mg |
| HYDROCHLORIC ACID | 0.004165 mL | 0.054145 mL |
| B-CYCLODEXTRIN SULFOBUTYLETHER, CAPTISOL ® | 200.0 mg | 2600 mg |
| SODIUM HYDROXIDE | QS | QS |
| WATER FOR INJECTION | QS 1.0 mL | QS 13.0 mL |
| NITROGEN | — | QS |

*QS is quantity sufficient as known to one of skill in the art.

Table B shows the stability of danirixin as formulated in Table A. This formulation required 5° C. storage for stability. Storage at this condition incurs higher costs and complexity of shipment and storage. At room temperature (25° C.), after two weeks the degradation impurity levels were already approaching the specification limit (0.2%). After only one week, degradation impurity levels of samples stored at 30° C. were approaching the specification limit (0.2%). In addition to the stability concerns of the free base formulation as illustrated by the data, a concern was the high quantity of sulfobutyl ether-β-cyclodextrin (CAPTISOL®) required to solubilize the API.

TABLE B

| | | Test | | |
|---|---|---|---|---|
| | | Danirixin Content by HPLC | Drug-related Impurities Content by HPLC (% area) | |
| Storage Condition | Time (Months) | (% Label Claim) (Mean) | Any Unqualified Impurity | Total Impurities |
| Initial | 0 | 98.8 | <0.05 | 2.0 |
| −20° C./AmbH Inverted | 1 | 98.5 | <0.05 | 1.6 |
| | 3 | 99.1 | <0.05 | 1.7 |
| 5° C./AmbH Inverted | 1 | 97.7 | <0.05 | 1.6 |
| | 3 | 99.1 | <0.05 | 1.7 |
| 25° C./60% RH Inverted | 1 week | 98.4 | 0.06, RRT$^5$ = 0.52 | 1.7 |
| | 2 weeks | 97.8 | 0.07, 0.10, 0.05, RRT = 0.52-0.54 | 1.9 |
| 30° C./65% RH Inverted | 1 week | 97.4 | 0.07, 0.11, 0.06, RRT = 0.52-0.53 | 1.9 |
| Freeze/Thaw Inverted | — | 98.0 | 0.06, RRT = 0.52 | 1.7 |

Example 2

IV Formulation of Lyophilized Hydrobromide Salt of Danirixin

Table C shows the components and respective amounts per IV formulation of the HBr lyophilized formulation of Danirixin.

TABLE C

| COMPOSITION (HBr lyophilized formulation) | Formula (mg/mL) 2 mg/mL | Unit Formula, Nominal Fill (mg/13 mL) |
|---|---|---|
| Danirixin, HBr. ACTIVE SUBSTANCE | 2.46 mg* | 31.98 mg |
| B-CYCLODEXTRIN SULFOBUTYLETHER, CAPTISOL ® | 40.0 mg | 520.0 mg |
| MANNITOL | 50 mg | 650.0 mg |
| CITRIC ACID | 0.655 mg | 8.515 mg |
| SODIUM CITRATE | 0.555 mg | 7.215 mg |
| SODIUM HYDROXIDE | QS | QS |
| HYDROCHLORIC ACID | QS | QS |
| pH | 3.9 | — |

*QS refers to "quantity sufficient" to fill the vial to the nominal fill (or volume).
*indicates 2 mg/mL that has been adjusted for the salt factor of 1.228 = 2.46 mg/mL A 2 mg/ml solution of danirixin HBr salt for lyophilization was made according to the below procedure.

A 10 mM pH4 citrate buffer is prepared. Mannitol (50 mg) is added to the buffer solution (0.5 mL) and mixed until dissolved. Sulfobutyl ether-β-cyclodextrin (CAPTISOL®) (40 mg) is added (50% of batch volume) and mixed until dissolved. 2 mg of the danirixin HBr is added to the solution and mixed until dissolved. The solution is brought to full batch volume with sterile water. The pH is adjusted to 3.5-4.5, using 1N NaOH or 1N HCl, as needed. The solution is filled into vials, lyophilized, purged with nitrogen and closed.

For reconstitution, sterile water is added to the vial and shaken until all material is dissolved. Reconstitution time is 15 seconds. pH holds around 4 after reconstitution.

Example 3

Lyophilization Cycle Development

Numerous lyophilization cycles can be evaluated in their ability to achieve the most efficient drying cycle. Variables often evaluated to effect the drying cycle include the freezing rate, primary drying temperature, time and pressure on the product. The current lyophilization process can be seen below in Table D.

TABLE D

| Step Name | Temperature (° C.) | Pressure (mT) | Ramp Rate (° C./min) | Hold Time (min) |
|---|---|---|---|---|
| Loading | Room Temp | — | — | 0 |
| Freezing | 5 | — | 1.5 | 30 |
| Freezing | −40 | — | 1.5 | 120 |
| Annealing | −10 | — | 1.5 | 180 |
| Freezing | −40 | — | 1.5 | 120 |
| Primary Drying | 5 | 200 | 1 | 1860 |
| Secondary Drying | 50 | 200 | 1 | 300 |

Example 4

Stability of the IV Formulation of Lyophilized Hydrobromide Salt of Danirixin Table E shows the stability of Danirixin as formulated in Example 2. This example shows the stability of this formulation with 4% sulfobutyl ether-β-cyclodextrin (CAPTISOL®) with no surfactants. The stability was measured as percent of impurity (Imp %) at multiple time points including: 1 week, 2 week, and 4 weeks, at various temperatures including: 5° C., 25° C., 40° C., and 50° C. and at 60% and 75% relative humidity (RH).

TABLE E

| | |
|---|---|
| Captisor ® | 4% |
| Surfactant | None |
| Impurity, Imp (%) Initial | 0.18 |
| Imp (%) 1 wk @ 40° C./75% RH | 0.28 |
| Imp (%) 1 wk @ 50° C./75% RH | 0.59 |
| Imp (%) 2 wk @ 5° C. | 0.19 |
| Imp (%) 2 wk @ 25° C./60% RH | 0.18 |
| Imp (%) 2 wk @ 40° C./75% RH | 0.36 |
| Imp (%) 2 wk @ 50° C./75% RH | 0.72 |
| Imp (%) 1M @ 5° C. | 0.18 |
| Imp (%) 1M @ 25° C./60% RH | 0.18 |
| Imp (%) 1M @ 40° C./75% RH | 0.55 |

The data in Table E shows that there is no increase in percentage of impurity when comparing 5° C. and 25° C. Furthermore, the prior statement extended to the 2 week and the 1 month time point. However, at the increased temperature, there was an increase in the impurity profile at all time points.

When taken together, the data provided in Table B on the stability of the freebase of IV formulation of danirixin and the data provided in Table E on the stability of the HBr IV formulation of danirixin, it can seen that the HBr IV formulation of danirixin offers an advantage in that it allows for room temperature storage, with a greatly improved shelf life, and lower amounts of sulfobutyl ether-β-cyclodextrin (CAPTISOL®).

REFERENCES

1) Morohashi, Mukaida. *J. Leukocyte Biol,* 1995. 57:180.
2) McColl, Clark-Lewis. *J. Immunology,* 1999, 163:2829.
3) Jones, Everard. *Eur Respir J* 2002; 20: 651-657.
4) Everard, Milner. *Archives of Disease in Childhood.* 1994; 71: 428-432.
5) Smith, Forsyth. 2001, *J. Paediatr. Child Health* 37:146.
6) McNamara, Smyth. *The Journal of Infectious Diseases* 2005; 191:1225-32.
7) Hull, Kwiatkowski. *Thorax* 2000; 55:1023-1027.
8) Goetghebuer, Hull. *Clin Exp Allergy* 2004; 34:801-803.
9) Waering. Sarawar. Viral Immunology, Volume 20, Number 3, 2007.
10) Tate, Reading. *Plos One.* March 2011, Volume 6, Issue 3.
11) Miller, Lukacs. *The Journal of Immunology,* 2003, 170: 3348-3356.
12) Sakai, Ochiai. *Journal of Virology.* March 2000, p. 2472-2476.

What is claimed is:

1. A pharmaceutical composition comprising:
   danirixin in its hydrobromide salt form; and one or more pharmaceutically acceptable excipients comprising: sulfobutyl ether-β-cyclodextrin, mannitol, and a citrate buffer.

2. The pharmaceutical composition according to claim 1, wherein danirixin has the structure:

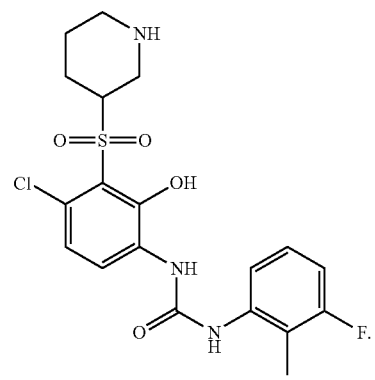 [SMILES: Cc1c(F)cccc1NC(=O)Nc1ccc(Cl)c(S(=O)(=O)C2CCCNC2)c1O]

3. The pharmaceutical composition according to claim 1, wherein danirixin has the structure:

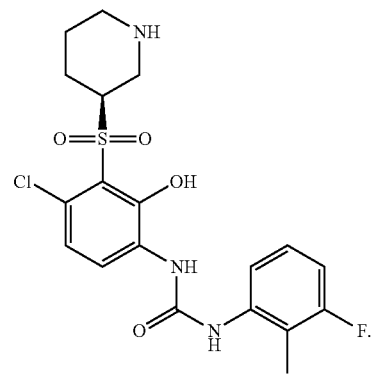 [SMILES: Cc1c(F)cccc1NC(=O)Nc1ccc(Cl)c(S(=O)(=O)[C@H]2CCCNC2)c1O]

4. The pharmaceutical composition according to claim 1, wherein the composition is an aqueous composition.

5. The pharmaceutical composition according to claim 1, wherein the composition is an aqueous composition suitable for intravenous administration.

6. The pharmaceutical composition according to claim 3, wherein the composition has a pH that ranges from 3.5 to 4.5.

7. The pharmaceutical composition according to claim 6, wherein the pH is about 4.

8. A process for the preparation of the pharmaceutical composition according to claim 1 comprising mixing danirixin with the excipients.

9. The pharmaceutical composition according to claim 6, which is freeze-dried to form a lyophilized powder.

10. A method of treating an infectious disease comprising administering to a subject in need thereof the pharmaceutical composition according to claim 1.

11. The method according to claim 10, wherein the infectious disease is a viral disease.

12. The method according to claim 11 wherein the infectious disease is influenza or respiratory syncytial virus.

13. The method according to claim 11, wherein the infectious disease is influenza.

14. The pharmaceutical composition according to claim 1 having the formulation as shown in the table below:

| COMPOSITION (HBr lyophilized formulation) | Formula (mg/mL) 2 mg/mL | Unit Formula, Nominal Fill (mg/13 mL) |
|---|---|---|
| Danirixin, HBr. ACTIVE SUBSTANCE | 2.46 mg* | 31.98 mg |
| B-CYCLODEXTRIN SULFOBUTYLETHER | 40.0 mg | 520.0 mg |
| MANNITOL | 50 mg | 650.0 mg |
| CITRIC ACID | 0.655 mg | 8.515 mg |
| SODIUM CITRATE | 0.555 mg | 7.215 mg |
| SODIUM HYDROXIDE | QS | QS |
| HYDROCHLORIC ACID | QS | QS |
| pH | 3.9 | — |

QS refers to "quantity sufficient" to fill the vial to the nominal fill (or volume);
*indicates 2 mg/mL that has been adjusted for the salt factor of 1.228 = 2.46 mg/mL.

* * * * *